United States Patent [19]

Grasselli et al.

[11] 4,001,317

[45] Jan. 4, 1977

[54] PROCESS FOR THE OXIDATION OF OLEFINS USING CATALYSTS CONTAINING VARIOUS PROMOTER ELEMENTS

[75] Inventors: Robert K. Grasselli, Chagrin Falls; Dev D. Suresh, Warrensville Heights; Harley F. Hardman, Lyndhurst, all of Ohio

[73] Assignee: The Standard Oil Company, Cleveland, Ohio

[22] Filed: July 22, 1974

[21] Appl. No.: 490,428

[52] U.S. Cl. .......................... 260/533 N; 252/462; 252/470; 260/604 R
[51] Int. Cl.² .................. C07C 51/32; C07C 45/04
[58] Field of Search .................... 260/533 N, 604 R

[56] References Cited

UNITED STATES PATENTS

| 3,642,930 | 2/1972 | Grasselli et al. | 260/533 N |
| 3,761,424 | 9/1973 | Koberstein et al. | 260/533 N |
| 3,825,502 | 7/1974 | Takenaka et al. | 260/604 R |
| 3,865,873 | 2/1975 | Oda et al. | 260/530 N |

FOREIGN PATENTS OR APPLICATIONS

| 2,000,425 | 7/1970 | Germany | 260/533 N |
| 47-38411 | 9/1972 | Japan | 260/533 N |
| 903,034 | 8/1962 | United Kingdom | 260/530 N |

*Primary Examiner*—Anton H. Sutto
*Attorney, Agent, or Firm*—Herbert D. Knudsen; Larry W. Evans; Gwenetta D. Hill

[57] ABSTRACT

The present invention is a process for the oxidation of olefins to unsaturated aldehydes and acids using a catalyst containing iron, bismuth, molybdenum plus at least one of nickel, cobalt, magnesium, zinc, cadmium or calcium and according to the invention, an element selected from germanium, cerium, thorium, manganese, niobium, chromium, praseodymium, yttrium, zirconium, ruthenium, gallium, tin, indium, copper, lanthanum, tantalum or tungsten. These catalysts may also contain certain elements that further enhance the desirability of the oxidation process.

5 Claims, No Drawings

PROCESS FOR THE OXIDATION OF OLEFINS USING CATALYSTS CONTAINING VARIOUS PROMOTER ELEMENTS

BACKGROUND OF THE INVENTION

The process for oxidizing olefins with various multi-component catalysts is known. Grasselli and Hardman, in U.S. Pat. No. 3,642,930 disclose that certain complex catalysts can be employed in the oxidation of olefins to obtain unsaturated aldehydes and acids. These catalysts indeed are very desirable for this oxidation reaction, but a continuous search has been made for other catalysts that would improve the results obtained with these catalysts of Grasselli and Hardman. The present invention is a result of such a search.

SUMMARY OF THE INVENTION

The invention is in the process for the preparation of unsaturated aldehydes and acids from propylene or isobutylene by the vapor phase oxidation of propylene or isobutylene with molecular oxygen at a temperature of about 200° to 600° C. in the presence of a catalyst, the improvement comprising using as the catalyst a catalyst of the formula $$X_a A_b D_c E_d Fe_f Bi_g Mo_{12} O_x$$

wherein
X is Ce, Th, Mn, Pr, Nb, Ge, Cr, Y, Zr, Ru, Ga, Sn, In, Cu, La, Ta, W or mixture thereof
A is an alkali metal, Tl or mixture thereof;
D is Ni, Co, Mg, Zn, Cd, Ca, Sr or mixture thereof;
E is P, As, B, S, Al or mixture thereof; and
wherein
$a$ is greater than 0 but less than 5;
$b$ and $d$ are 0–4;
$c$, $f$ and $g$ are 0.1–12; and
$x$ is the number of oxygens required to satisfy the valence requirements of the other elements present.

This oxidation reaction gives especially desirable results at atmospheric or superatmospheric pressure.

The central aspect of the present invention is the particular catalyst employed. The catalysts may be any of the catalysts delimited by the formula described above. In the preferred practice of the invention each of the elements described by X is separately incorporated into the catalyst. This is conveniently accomplished by setting X independently equal to the various elements. Also preferred as far as the broad compositional structure of the catalyst is concerned are those catalysts that contain potassium, rubidium, cesium or mixture thereof and those catalysts that contain nickel, cobalt or mixture thereof.

The catalysts of the invention are prepared by techniques that are broadly known in the art. These techniques include the coprecipitation of soluble salts. More specific information on the preparation of the catalysts is given in the Specific Embodiments.

The catalysts of the invention may be used in the supported or unsupported form. Suitable support materials include silica, alumina, Alundum, titania, zirconia, silicon carbide and the like. The catalysts may also be used in various physical forms. The catalysts can be employed in a fixed-bed reactor or a fluid-bed reactor.

The process for oxidation of propylene or isobutylene is well known in the art. Broadly, a mixture of the olefin and molecular oxygen, optionally in the presence of steam or other diluent, is contacted with a catalyst at an elevated temperature of about 200°–600° C. for a contact time sufficient to convert the olefin to the corresponding unsaturated aldehyde and acid. Normally, the product from these reactions contains a very large portion of the aldehyde and a smaller by-product amount of the unsaturated acid. The contact time may vary widely from a few seconds to a number of seconds or more. The reaction can be conducted under atmospheric, superatmospheric or subatmospheric pressure with the use of a superatmospheric pressure normally being used on a commercial scale.

One special advantage of the catalysts of the invention is their ability to withstand the feed of large amounts of olefin over the catalyst in a given time. This is normally measured in terms of WWH which is the weight of olefin per weight of catalyst per hour. In other words, these catalysts can efficiently work on large amounts of olefin. Catalysts found in this art tend to be less efficient when large amounts of olefin are fed in a given period of time.

SPECIFIC EMBODIMENTS

EXAMPLE 1–8

Oxidation of Isobutylene at Atmospheric Pressure

Various catalysts of the invention containing 20% $SiO_2$ were prepared by the procedures described below.

EXAMPLE 1

$$Pr_{0.5}K_{0.1}Ni_{2.5}Co_{4.5}Fe_3BiMo_{12}O_x$$

A slurry of 63.56 g. of $(NH_4)_6Mo_7O_{24}\cdot4H_2O$, 52.33 g. Nalco 40% silica sol and 2.60 g. $PrO_2$ was prepared. Separately, a solution of 36.36 g. $Fe(NO_3)_3\cdot9H_2O$, 14.55 g. $Bi(NO_3)_3\cdot5H_2O$, 39.29 g. $Co(NO_3)_2\cdot6H_2O$, 21.80 g. $Ni(NO_3)_2\cdot6H_2O$ and 3.03 g. of a 10% solution of $KNO_3$ was prepared. The slurry and solution were combined, the liquid evaporated to a paste and the paste was dried at 120° C. overnight. The catalyst was heat treated at 290° C. for 3 hours, at 425° C. for three hours and at 550° C. for 16 hours.

EXAMPLES 2–5

The catalysts were prepared in the same manner as described above except that the appropriate amount of the nitrates of manganese and thorium, the chloride of germanium and the oxide of niobium were added in place of the praseodymium.

EXAMPLE 6

$$Mn_{0.5}Cs_{0.5}K_{0.5}Ni_{2.5}Co_{4.5}Fe_3BiMo_{12}O_x$$

A solution of 2.72 g. $CsNO_3$, 1.19 g. $KNO_3$, 20.33 g. $Ni(NO_3)_2\cdot6H_2O$, 36.61 g. $Co(NO_3)_2\cdot6H_2O$, 33.9 g. $Fe(NO_3)_3\cdot9H_2O$ 13.6 g. $Bi(NO_3)_3\cdot5H_2O$ was added to a slurry of 2.5 g. $Mn(NO_3)_2$, 59.2 g. $(NH_4)_6Mo_7O_{24}\cdot4H_2O$ and 50 g. Nalco 40% silica sol. The mixture was evaporated, dried and heat treated as shown in Example 1.

EXAMPLES 7–8

The catalysts were prepared in the same manner except that the 1.46 g. $GeO_2$ or 1.84 g. $Nb_2O_5$ was added instead of the manganese nitrate.

In a fixed-bed reactor, constructed of a 0.75 cm. inside diameter stainless steel tube, was placed 5 cc. of each of the catalysts prepared above. These catalysts were tested at a reaction temperature of 371° C. using a feed of isobutylene/air/steam of 1/10/4 and an apparent contact time of 3.3 seconds. The results of these experiments are given in Table 1. The results are stated as follows:

$$\% \text{ yield per pass} = \frac{\text{moles of product} \times 100}{\text{moles of isobutylene fed}}$$

$$\% \text{ conversion} = \frac{\text{moles of isobutylene reacted} \times 100}{\text{moles of isobutylene fed}}$$

$$\% \text{ selectivity} = \frac{\text{moles of product formed} \times 100}{\text{moles of isobutylene reacted}}$$

In the Tables MA is methacrolein, and MAA is methacrylic acid.

Table 1

Oxidation of Isobutylene to Methacrolein and Methacrylic Acid at Atmospheric Pressure Using a Catalyst of $YNi_{2.5}Co_{4.5}Fe_3BiMo_{12}O_x$

| | | Results, % | | | | |
|---|---|---|---|---|---|---|
| | | Yield Per Pass | | | Conver- | Select- |
| Example | Catalyst, Y = | MA | MAA | Total | sion | ivity |
| 1 | $Pr_{0.5}K_{0.1}$ | 61.6 | 2.2 | 63.8 | 91.3 | 69.9 |
| 2 | $Mn_{0.5}K_{0.1}$ | 68.5 | 2.9 | 71.4 | 100.0 | 71.4 |
| 3 | $Ge_{0.5}K_{0.1}$ | 67.0 | 4.5 | 71.5 | 100.0 | 71.5 |
| 4 | $Nb_{0.5}K_{0.1}$ | 52.2 | 2.5 | 54.7 | 82.9 | 66.1 |
| 5 | $Th_{0.5}K_{0.1}$ | 74.3 | 2.6 | 76.9 | 100.0 | 76.9 |
| 6 | $Mn_{0.5}Cs_{0.5}K_{0.5}$ | 68.3 | 3.4 | 71.7 | 100.0 | 71.7 |
| 7 | $Ge_{0.5}Cs_{0.5}K_{0.5}$ | 77.1 | 1.0 | 78.1 | 94.3 | 82.9 |
| 8 | $Nb_{0.5}Cs_{0.5}K_{0.5}$ | 75.3 | 1.2 | 76.5 | 94.7 | 80.8 |

EXAMPLES 9–13

Oxidation of Isobutylene at Superatmospheric Pressure

In the same manner as described above, various catalysts prepared above were used in reactions at superatmospheric pressure. The catalysts were prepared as follows:

EXAMPLE 9

$Cr_{0.5}Cs_{0.5}Ni_{2.5}Co_{4.5}Fe_3BiMo_{12}O_x$

A solution of 1.1 g. $CsNO_3$, 8.2 g. $Ni(NO_3)_2 \cdot 6H_2O$, 14.8 g. $Cs(NO_3)_2 \cdot 6H_2O$, 13.7 g. $Fe(NO_3)_3 \cdot 5H_2O$, 5.5 g. $Bi(NO_3)_3 \cdot 5H_2O$, 2.3 g. $Cr(NO_3)_3 \cdot 9H_2O$ was prepared and a slurry of 23.9 g. $(NH_4)_6Mo_7O_{24} \cdot 4H_2O$ and 20 g. Nalco 40% silica was added. The catalyst was dried and heated at 430° C. for 4 hours and 600° C. for 3 hours.

EXAMPLES 10–13

These catalysts were prepared in the same manner as Example 9 using the appropriate ingredients as starting materials.

The pressure, unless otherwise noted, at 12 p.s.i.g. The temperature of the reaction and the results are shown in Table 2. The feed was of the same composition as described above and the apparent contact time was 3.5–4.1 seconds and the WWH was 0.098–0.159.

Table 2

Oxidation of Isobutylene to Methacrolein and Methacrylic Acid at Superatmospheric Pressure in the Presence of a Catalyst of $YNi_{2.5}Co_{4.5}Fe_3BiMo_{12}O_x$

| | | | Results, % | | | |
|---|---|---|---|---|---|---|
| Example | Catalyst, Y = | Temp., ° C. | MA | MAA | Total | Conversion | Selectivity |
| 9 | $Cr_{0.5}Cs_{0.5}$ | 371 | 58.9 | 2.9 | 61.8 | 81.7 | 75.6 |
| 10 | $Ge_{0.5}Cs_{0.5}$ | 371 | 68.4 | 5.6 | 74.0 | 96.5 | 76.7 |
| 11 | $Mn_{0.5}Cs_{0.1}$ | 343 | 64.5 | 4.8 | 69.3 | 99.6 | 69.5 |
| 12 | $Th_{0.5}Cs_{0.5}$ | 343 | 61.5 | 3.5 | 65.0 | 89.0 | 73.0 |
| 13 | $Ce_{0.5}Cs_{0.2}$ | 363 | 70.3 | 6.4 | 76.7 | 98.9 | 77.6 |

EXAMPLE 14

Preparation of Acrolein

In the same manner as shown in the examples above, acrolein and acrolein and acrylic acid were prepared from propylene. The catalyst was 80% $Ge_{0.5}K_{0.1}Ni_{2.5}Co_{4.5}Fe_3BiMo_{12}O_x$ + 20% $SiO_2$. The catalyst was heat treated at 550° C. for 16 hours. Five cc. of the catalyst was employed, the reaction temperature was 350° C. and the apparent contact time was 2.5 seconds. The feed of propylene/air/steam was 1/11/4. The single pass yield of acrolein was 84.8%, the single pass yield to acrylic acid was 5.2%, the conversion of the propylene was 93.0% and the selectivity to acrolein and acrylic acid was 96.8%.

We claim:

1. In the process for the preparation of unsaturated aldehydes and acids from propylene or isobutylene by the vapor phase oxidation of propylene or isobutylene with molecular oxygen at a temperature of about 200° to 600° C. in the presence of a catalyst, the improvement comprising using as the catalyst a catalyst of the formula $$Ce_a \, A_b \, D_c \, E_d \, Fe_f \, Bi_g \, Mo_{12} \, O_x$$

wherein
A is an alkali metal, Tl or mixture thereof;
D is Ni, Co, Mg, Zn, Cd, Ca, Sr or mixture thereof;
E is P, As, B, S, Al or mixture thereof;
and wherein
a is greater than 0 but less than 5;
b and d are 0–4;
c, f and g are 0.1–12; and
x is the number of oxygens required to satisfy the valence requirements of the other elements present.

2. In the process for the preparation of unsaturated aldehydes and acids from propylene or isobutylene by the vapor phase oxidation of propylene or isobutylene with molecular oxygen at a temperature of about 200° to 600° C. in the presence of a catalyst, the improvement comprising using as the catalyst a catalyst of the formula $$Th_a \, A_b \, D_c \, E_d \, Fe_f \, Bi_g \, Mo_{12} \, O_x$$

wherein
A is an alkali metal, Tl or mixture thereof;
D is Ni, Co, Mg, Zn, Cd, Ca, Sr or mixture thereof;

E is P, As, B, S, Al or mixture thereof;
and wherein
- $a$ is greater than 0 but less than 5;
- $b$ and $d$ are 0–4;
- $c, f$ and $g$ are 0.1–12; and
- $x$ is the number of oxygens required to satisfy the valence requirements of the other elements present.

3. In the process for the preparation of unsaturated aldehydes and acids from propylene or isobutylene by the vapor phase oxidation of propylene or isobutylene with molecular oxygen at a temperature of about 200° to 600° C. in the presence of a catalyst, the improvement comprising using as the catalyst a catalyst of the formula

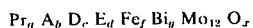

$$Pr_a\ A_b\ D_c\ E_d\ Fe_f\ Bi_g\ Mo_{12}\ O_x$$

wherein
- A is an alkali metal, Tl or mixture thereof;
- D is Ni, Co, Mg, Zn, Cd, Ca, Sr or mixture thereof;
- E is P, As, B, S, Al or mixture thereof;

and wherein
- $a$ is greater than 0 but less than 5;
- $b$ and $d$ are 0–4;
- $c, f$ and $g$ are 0.1–12; and
- $x$ is the number of oxygens required to satisfy the valence requirements of the other elements present.

4. In the process for the preparation of unsaturated aldehydes and acids from propylene or isobutylene by the vapor phase oxidation of propylene or isobutylene with molecular oxygen at a temperature of about 200° to 600° C. in the presence of a catalyst, the improvement comprising using as the catalyst a catalyst of the formula

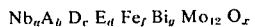

$$Nb_a\ A_b\ D_c\ E_d\ Fe_f\ Bi_g\ Mo_{12}\ O_x$$

wherein
- A is an alkali metal, Tl or mixture thereof;
- D is Ni, Co, Mg, Zn, Cd, Ca, Sr or mixture thereof;
- E is P, As, B, S, Al or mixture thereof;

and wherein
- $a$ is greater than 0 but less than 5;
- $b$ is greater than 0 but less than 4;
- $d$ is 0 to 4;
- $c, f$ and $g$ are 0.1–12; and
- $x$ is the number of oxygens required to satisfy the valence requirements of the other elements present.

5. In the process for the preparation of unsaturated aldehydes and acids from propylene or isobutylene by the vapor phase oxidation of propylene or isobutylene with molecular oxygen at a temperature of about 200° to 600° C. in the presence of a catalyst, the improvement comprising using as the catalyst a catalyst of the formula

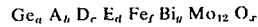

$$Ge_a\ A_b\ D_c\ E_d\ Fe_f\ Bi_g\ Mo_{12}\ O_x$$

wherein
- A is an alkali metal, Tl or mixture thereof;
- D is Ni, Co, Mg, Zn, Cd, Ca, Sr or mixture thereof;
- E is P, As, B, S, Al or mixture thereof;

and wherein
- $a$ is greater than 0 but less than 5;
- $b$ is greater than 0 but less than 4;
- $d$ is 0 to 4;
- $c, f$ and $g$ are 0.1–12; and
- $x$ is the number of oxygens required to satisfy the valene requirements of the other elements present.

* * * * *

UNITED STATES PATENT OFFICE
CERTIFICATE OF CORRECTION

PATENT NO. : 4,001,317
DATED : January 4, 1977
INVENTOR(S) : Robert K. Grasselli et al.

It is certified that error appears in the above-identified patent and that said Letters Patent are hereby corrected as shown below:

Column 2: Line 26, "Example" should be ---Examples---

Column 6: Line 35, "valene" should be --valence--

Signed and Sealed this

Twenty-seventh Day of December 1977

[SEAL]

Attest:

RUTH C. MASON
*Attesting Officer*

LUTRELLE F. PARKER
*Acting Commissioner of Patents and Trademarks*